(12) United States Patent
Wasser et al.

(10) Patent No.: US 6,372,964 B1
(45) Date of Patent: Apr. 16, 2002

(54) FOR HIGHER BASIDIOMYCETES MUSHROOMS GROWN AS BIOMASS IN SUBMERGED CULTURE

(75) Inventors: Solomon P. Wasser, Haifa; Sergey V. Reshetnikov, Kiev; Elvira F. Solomko, Kiev; Asya S. Buchalo, Kiev, all of (UA); Eviatar Nevo, Haifa (IL)

(73) Assignee: Med_Myco Ltd., Haifa (IL)

( * ) Notice: Subject to any disclaimer, the term of this patent is extended or adjusted under 35 U.S.C. 154(b) by 0 days.

(21) Appl. No.: 09/432,653

(22) Filed: Nov. 2, 1999

(51) Int. Cl.$^7$ .............................................. A01H 15/00
(52) U.S. Cl. .............................. 800/297; 47/1.1; 71/5; 426/7; 260/112.5
(58) Field of Search ................ 47/1.1; 71/5; 260/112.5; 426/7; 800/297

(56) References Cited

U.S. PATENT DOCUMENTS 4,333,757 A    6/1982  Kurtzman, Jr. .................. 71/5
4,810,504 A *  3/1989  Schindler ........................ 426/7
5,934,012 A *  8/1999  Holtz et al. ..................... 47/1.1

OTHER PUBLICATIONS

Zadrazil, F., Cultivation of Pleurotus; The Biology and Cultivation of Edible Mushrooms; pp. 521–557, 1978.*
Hum Feld et al., Mushroom Mycelium Production By Submerged Propagation; Food Technology; vol. 3, No. 11, pp. 355–356, 1949.*
Hawksworth DL et al. 1995, in Ainsworth & Bisbi's Dictionary of the Fungi, $8^{th}$ Ed CAB International, University Press, Cambridge.

* cited by examiner

Primary Examiner—Bruce R. Campell
Assistant Examiner—Kent L. Bell
(74) Attorney, Agent, or Firm—Rashida A. Karmali (57) ABSTRACT

The present invention describes new and distinct horticultural varieties of higher Basidiomycetes mushrooms grown in submerged culture. Specifically, the new varieties of species of the genus Pleurotus offer superior yields of mushroom cell biomass and greater concentrations of the protein rich in essential amino acids, fatty acids, vitamins and minerals.

2 Claims, 12 Drawing Sheets

FOR HIGHER BASIDIOMYCETES MUSHROOMS GROWN AS BIOMASS IN SUBMERGED CULTURE

FIELD OF THE INVENTION

The present invention is directed to new and distinct strains of the higher Basidiomycetes edible mushrooms which are adapted to grow in biomass form in submerged culture containing especially formulated nutrients.

BACKGROUND OF THE INVENTION

Edible higher Basidiomycetes mushrooms have been used in folk medicine since ancient times. They include species from the Basidiomycetes class that have macroscopic fruit bodies, also known as basidioma or basidiocarp. These fruit bodies can be either hypogeous or epigeous, large enough to be seen with the naked eye, and can be picked by hand. Higher Basidiomycetes contain approximately 10,000 species from 550 genera and 80 families. The distinguishing characteristic of Basidiomycetes is the presence of basidium leaving exogenous basidiospores as a result of meiothic process.

The typical life cycle involves the germination of the basidiospore to give a primary haploid mycelium, which in turn becomes a secondary mycelium. Nuclear fusion takes place in the young basidium and meiosis takes place before basidiospore development. The macroscopic basidioma is generally fleshy and takes a variety of forms including terrestrial or hypogeneous, lignicolous or saprobic, mycorrhizal or pathogenic, edible, medicinal, hallucinogenic or poisonous mushrooms. Hawksworth D.L. et al, 1995, in Ainsworth & Bisbi's Dictionary of the Fungi, 8th ed. CAB International, University Press, Cambridge p. 616.

The most popular species of cultivated edible mushrooms include *Agaricus bisporus* (J Lge) Imbach, *A. bitorquis* (Quél.) Sacc, *Lentinus edodes* (Berk) Sing., Pleurotus spp., Auricularia spp., *Volvariella volvacea* (Fr) Sing., *Flammulina velutipes* (Fr.) Sing., *Tremella fuciformis* Berk., *Hypsizygus marmoreus* (Peck) Bigel., *Pholita nameko* (T. Ito) S. Ito et Imai, *Grifola frondosa* (Dicks.: Fr.) S.F. Gray, *Hericium erinaceus* (Bull: Fr.) Pers., *Dictyophora indusiata* (Vent.: Pers.) Fischer, *Stropharia rugosoannulata* Farl. apud Murr., *Lepista nuda* (Bull.: Fr.) Cooke, *Agrocybe aegerita* (Brig.) Sing., *Pleurotus citrinopileatus* Sing. In 1994, the world production of cultivated edible mushrooms was estimated to be approximately five million tons, which was valued at about ten billion dollars (US).

The cultivation of fruiting bodies of mushrooms deals with living organisms, for example, the mushroom itself and other microorganisms which may either be harmful or beneficial. Therefore, the methods employed in mushroom cultivation require modifications depending upon the region being cultivated, substrates available, environmental conditions and species of microorganisms encountered. The cultivation of mushrooms for fruit bodies production is a long-term process needing from one to several months for the first fruiting bodies to appear. In the present invention, the growth of pure mushroom cultures in submerged conditions on a liquid culture media permits to accelerate their growth, resulting in large biomass yields within a few days. Optimization of the culture medium composition and physicochemical conditions of growth allows regulation of fungal metabolism, and in turn obtain high yields of the biomass. It also allows production of large amounts of specific mushrooms which are rich in specific medicinal components and/or others nutritional substances of constant composition.

The data are obtained on the quantitative chemical composition and identity of submerged mycelial biomass and carpophores in varieties of higher Basidiomycetes mushrooms.

SUMMARY OF THE INVENTION

The present invention is directed towards higher Basidiomycetes mushrooms of the genus Pleurotus grown in submerged culture on nutrient media. The outstanding characteristics of these higher Basidiomycetes mushrooms growing as a biomass in submerged cultures are their shorter incubation period within a few days in the nutrient media comparing with standard fruiting Basidiomycetes mushroom varieties, and the increased yields of biologically active compounds such as protein rich in the essential amino acids and vitamins serving as functional foods compared with the yield of these components in carpophores of the standard fruiting Basidiomycetes mushrooms.

BRIEF DESCRIPTION OF THE ILLUSTRATIONS

BOTANICAL DESCRIPTION

Figure 1:
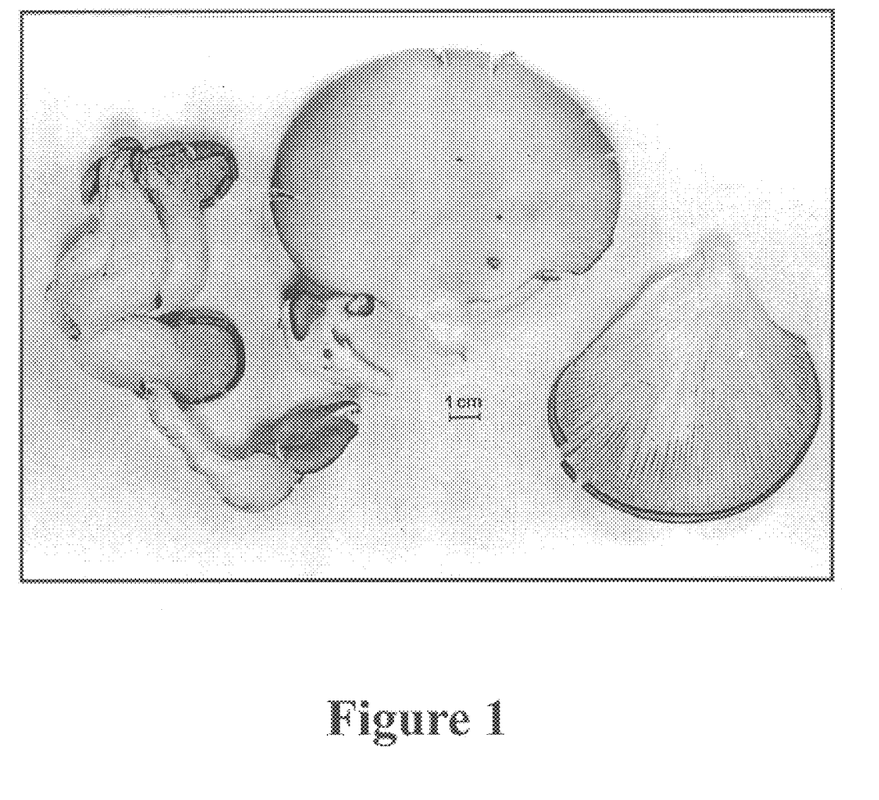
FIG. 1 shows a top view of the cultivated mushroom *Pleurotus ostreatus* CBS 101937 fruiting bodies.
Figure 2:
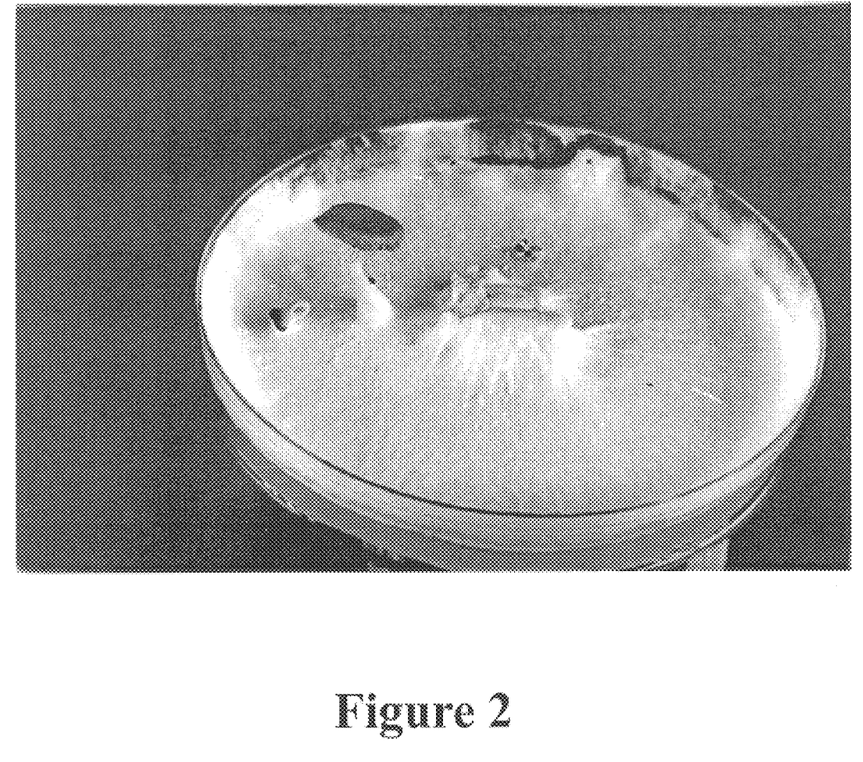
FIG. 2 shows a view of *Pleurotus ostreatus* CBS 101937 fruiting in the petri dish with malt agar medium.
Figure 3:
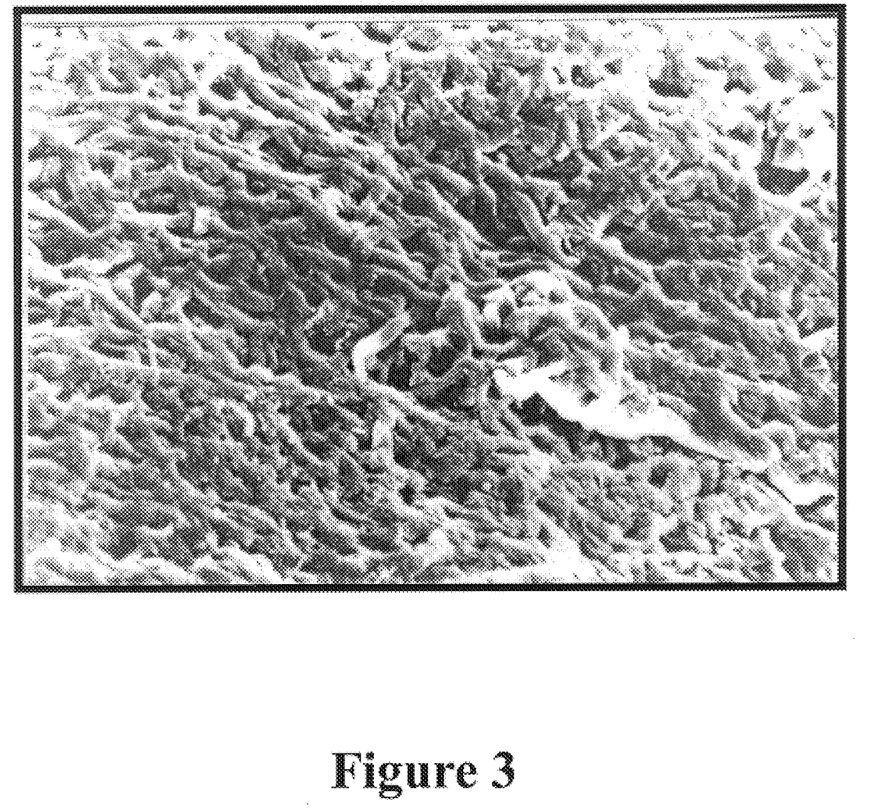
FIG. 3 shows a surface of submerged culture pellet of *Pleurotus ostreatus* CBS 101937. Scanning electron microscopy (SEM),×1500.
Figure 4:
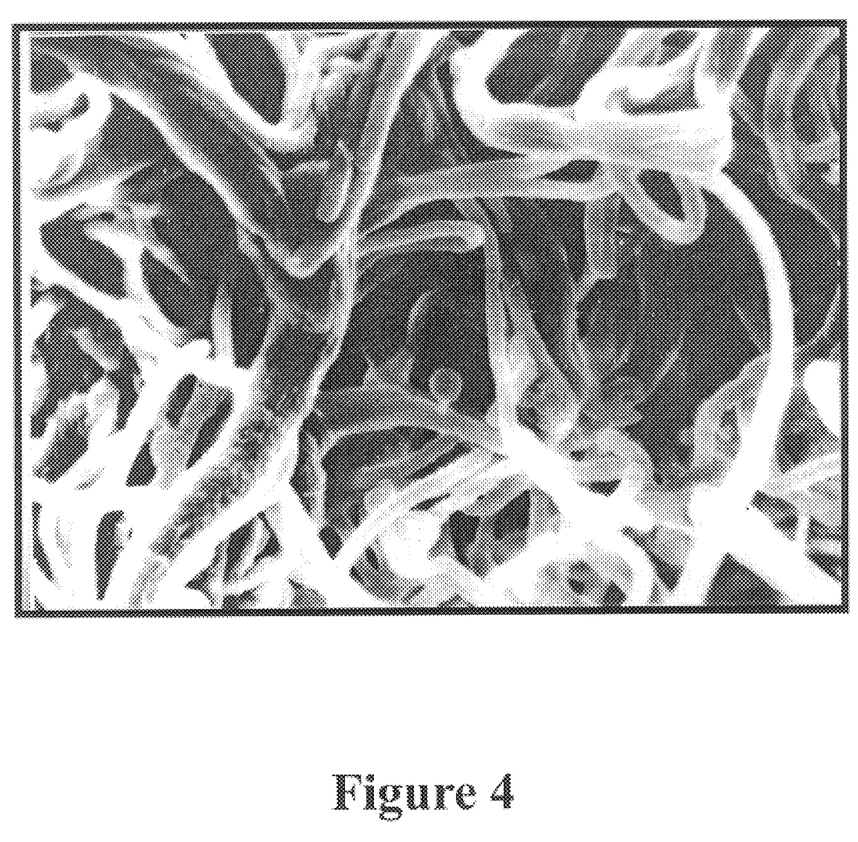
FIG. 4 shows a part of a surface of submerged culture pellet of *Pleurotus ostreatus* CBS 101937.SEM,×3000.
Figure 5:
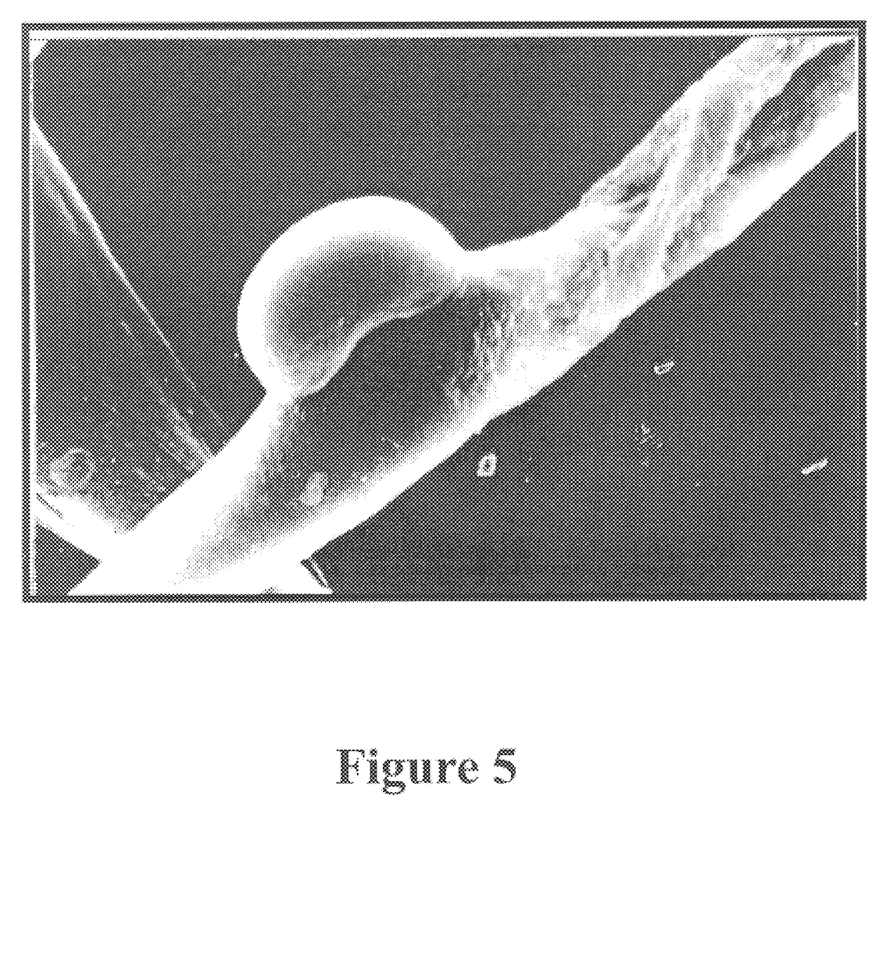
FIG. 5 shows a single clamp connection on a hypha of *Pleurotus ostreatus* CBS 101937, typical for Basidiomycetes. SEM,×4000.
Figure 6:
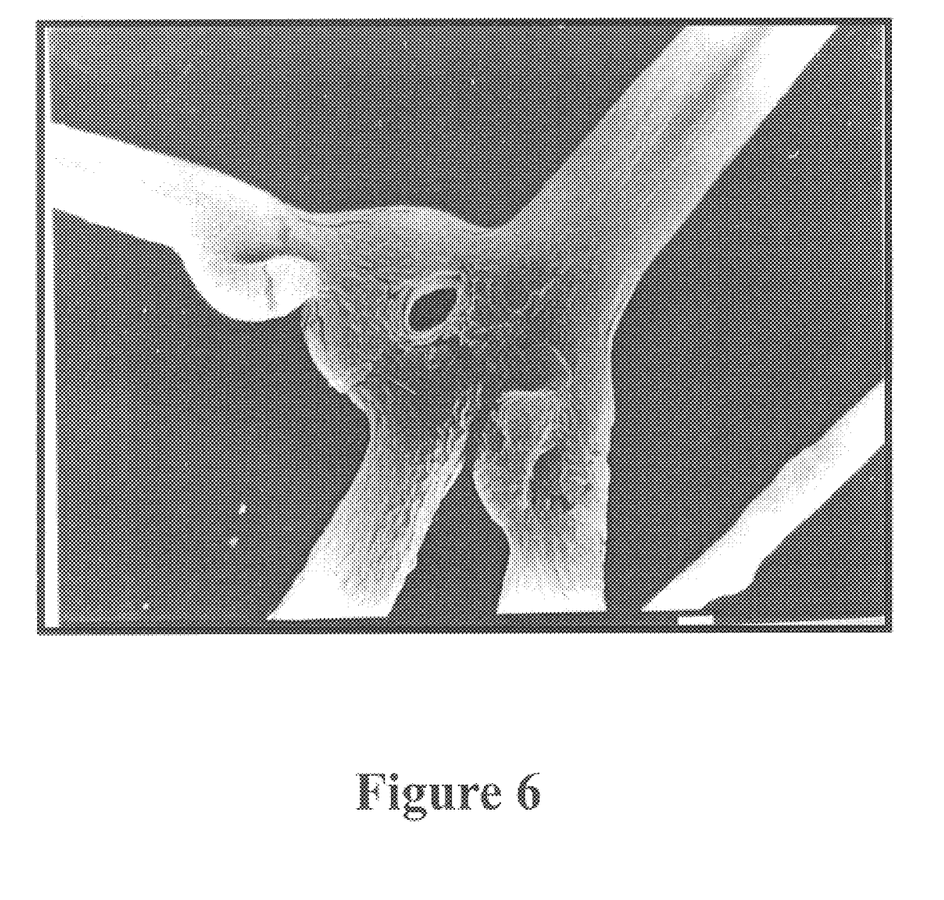
FIG. 6 shows a clamp connection on a *Pleurotus ostreatus* CBS 101937 hypha proliferating by new hyphae with clamps. SEM,×4800.
Figure 7:
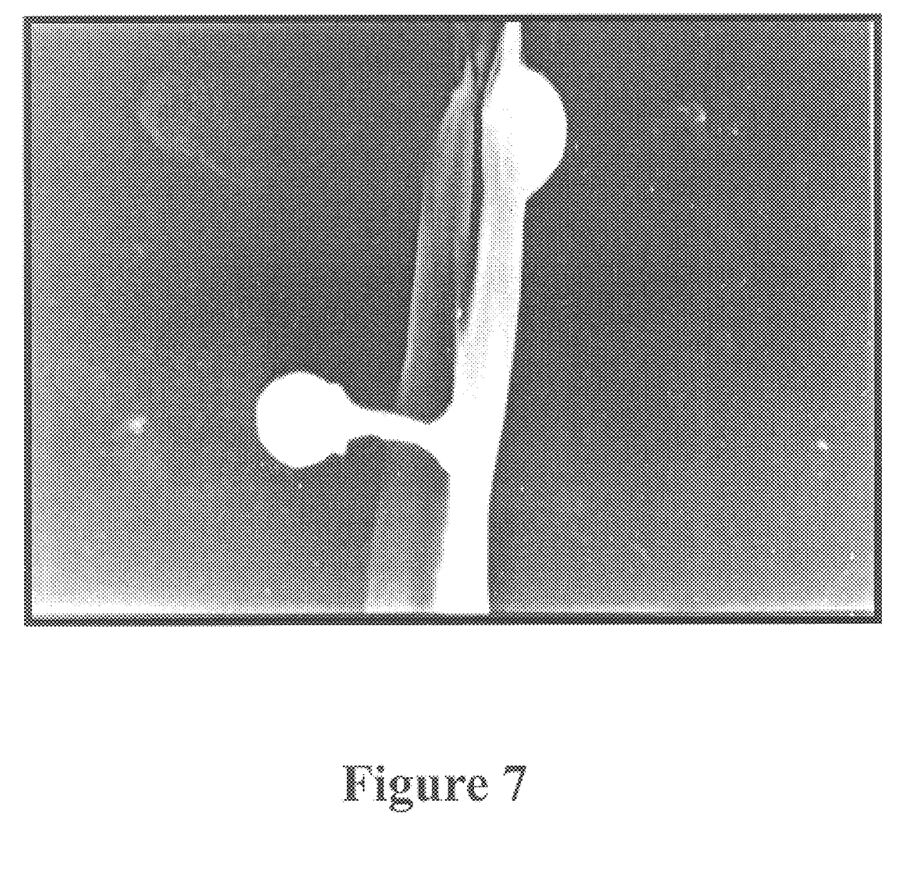
FIG. 7 shows a conidium-like structure on a hypha of *Pleurotus ostreatus* CBS 101937, a typical for the genus Pleurotus. SEM,×6000.
Figure 8:
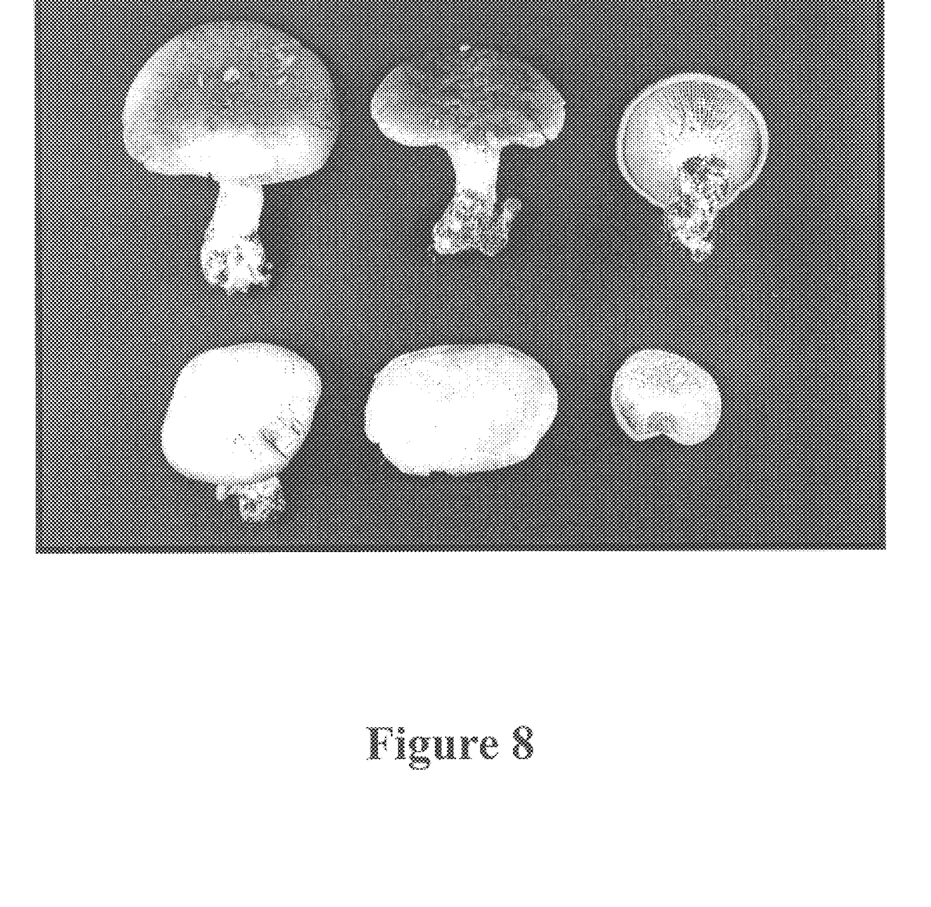
FIG. 8 shows a top view of the *Pleurotus eryngii* var. *ferulae* fruiting bodies.
Figure 9:
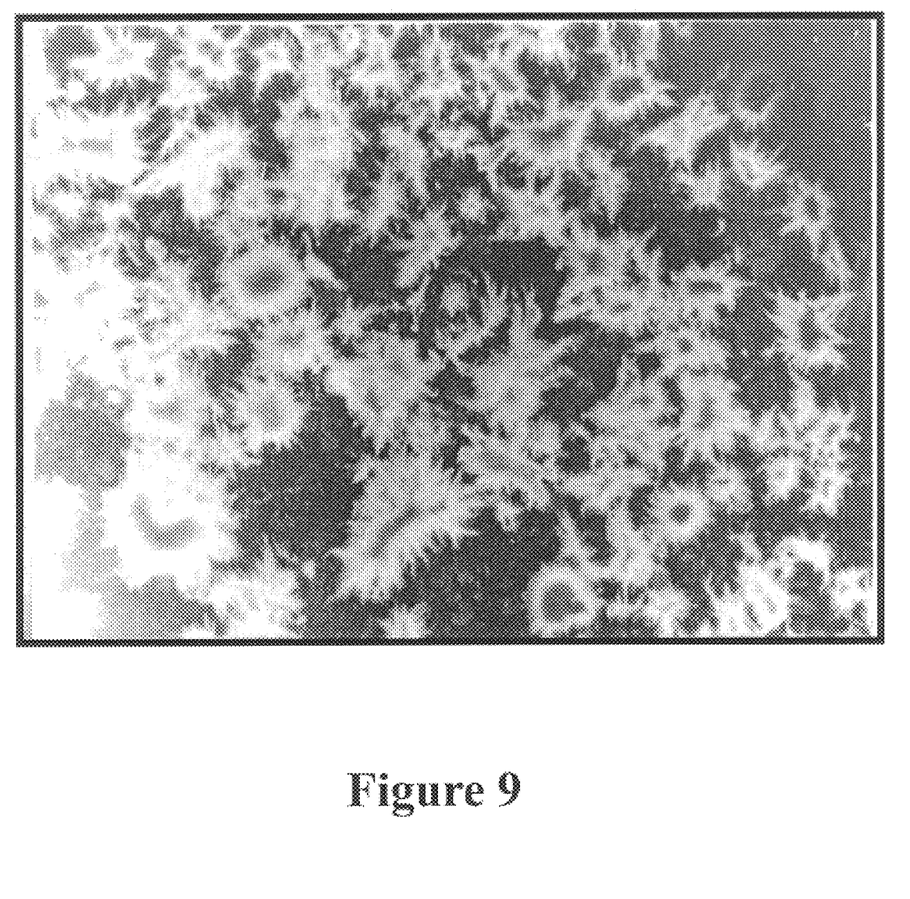
FIG. 9 shows a view of *Pleurotus eryngii* var. *ferulae* CBS 101938 submerged culture biomass in the form of pellets. Magnification×10.
Figure 10:
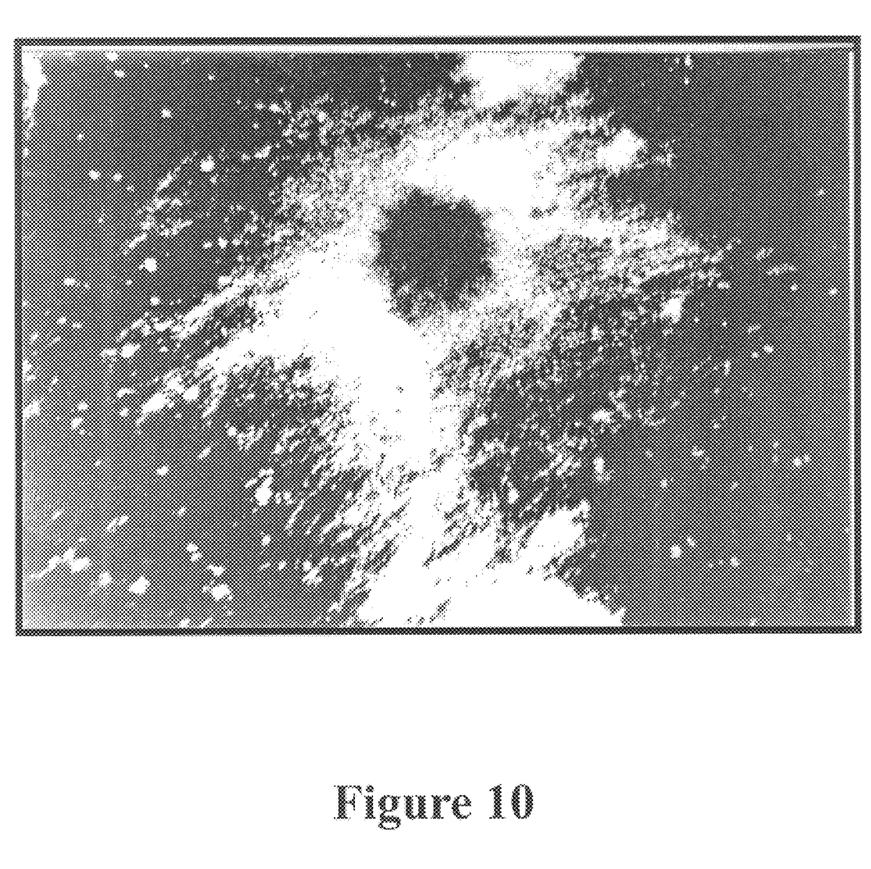
FIG. 10 shows a view of *Pleurotus eryngii* var. *ferulae* CBS 101938 submerged culture biomass in the form of pellets. Magnification×40.
Figure 11:
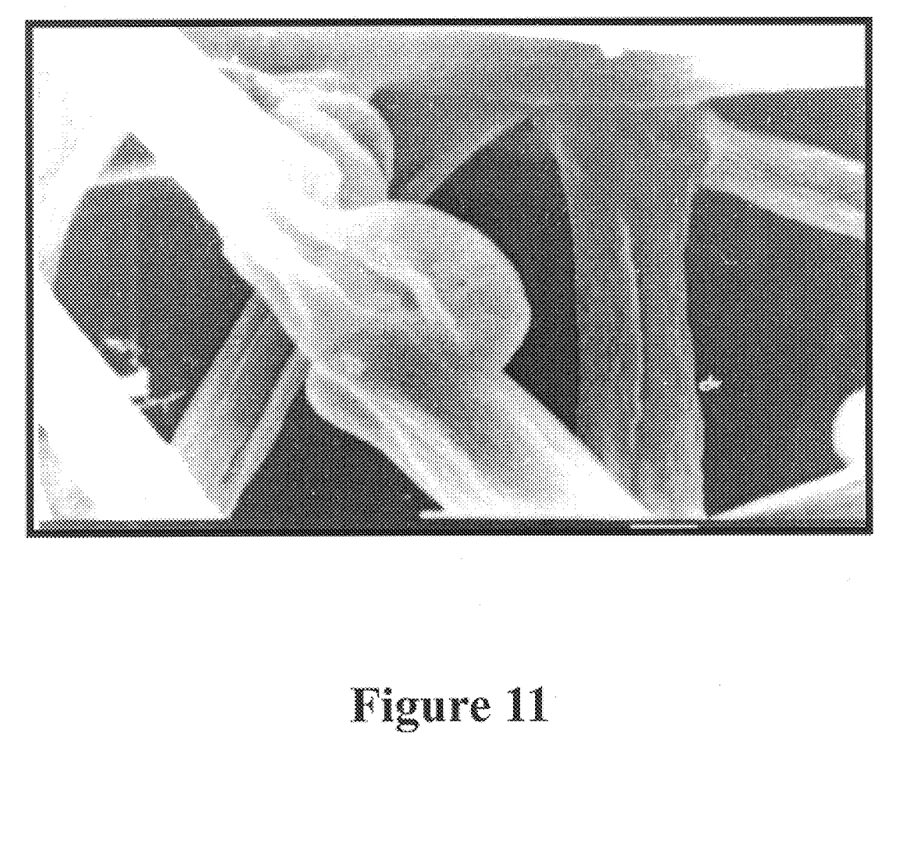
FIG. 11 shows a single clamp connection on a hypha of *Pleurotus eryngii* var. *ferulae* CBS 101938, typical for Basidiomycetes. SEM,×7800.
Figure 12:
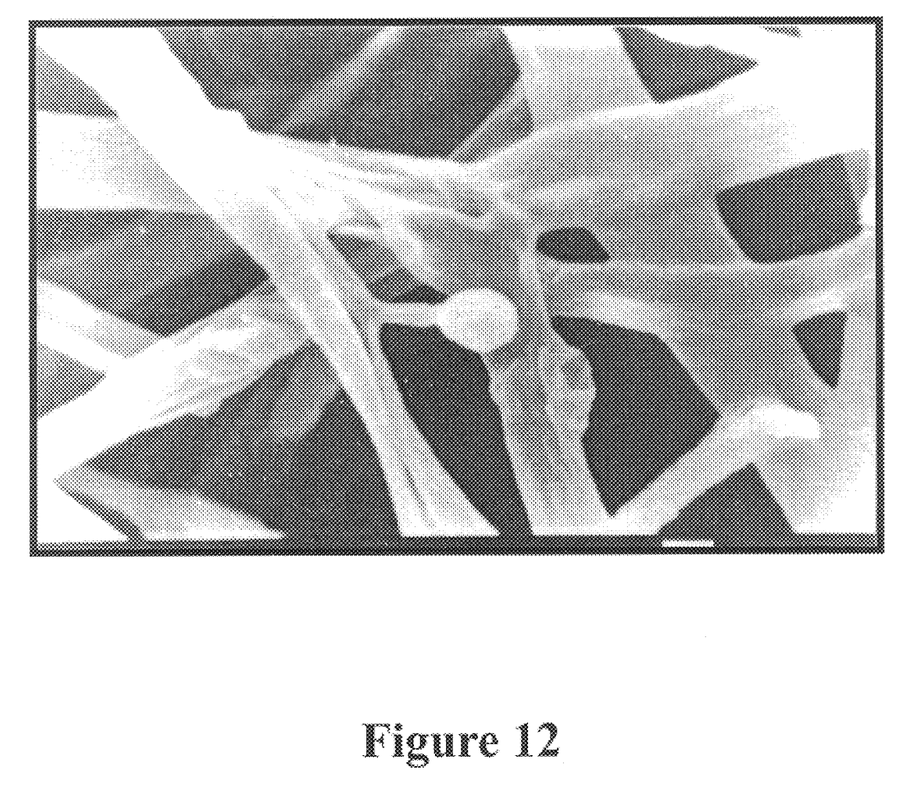
FIG. 12 shows a conidium-like structure on a hypha of *Pleurotus eryngii* var. *ferulae* CBS 101938, typical for the genus Pleurotus. SEM,×6000.

The following two species of the higher Basidiomycetes mushrooms have been deposited as cultures with the Centraalbureau voor Schimmelcultures (CBS), Oosterstraat 1. Postbus 273, NL 3740 AG Baarn. The Netherlands, on Jun. 14, 1999: *Pleurotus ostreatus* as Acc. No. CBS 101937 and *Pleurotus eryngii* var. *ferulae* as Acc. No. CBS 101938 under the Terms of the Budapest Treaty. These are representative embodiments and in no way restrict the scope of the claims of the invention. The following descriptions are of the higher Basidiomycetes mushrooms of the genus Pleurotus grown in submerged culture. When these Basidiomycetes mushrooms are grown under different conditions, it will be obvious that their appearance may be difficult from that described herein.

Table 1 describes the general composition of the *P. ostreatus* CBS 101937 fruiting bodies and submerged mycelium (% dry weight), and specifically for carbohydrates, crude fiber, crude protein, lipids and ash. The carbohydrate level in the mycelium biomass is lower and the crude protein level is higher than the respective levels in fruting bodies.

TABLE 1

| General nutrients | Fruiting bodies | Mycelium |
| --- | --- | --- |
| Total carbohydrate | 57.0–65.0 | 41.0–58.0 |
| Crude fiber | 6.5–8.3 | 5.0–5.3 |
| Crude protein | 22.0–41.0 | 21.0–48.0 |
| Total lipids | 2.2–7.2 | 2.0–7.2 |
| Ash | 6.1–10.7 | 4.2–7.9 |

Table 2 describes the crude protein content and the amino acid composition of the *P. ostreatus* CBS 101937 submerged mycelium (g/100 g crude protein). The crude protein level and the total essential amino acid content in the *P. ostreatus* CBS 101937 submerged mycelium than in the fruiting bodies.

TABLE 2

| Amino Acids | Fruiting bodies | Mycelium |
| --- | --- | --- |
| Crude Protein (% dry weight) | 16.0–18.0 | 35.3–42.0 |
| Tryptophan | 1.1–1.2 | 0.7–0.8 |
| Lysine | 6.7–8.1 | 4.6–7.0 |
| Threonine | 2.8–3.8 | 3.1–3.5 |
| Valine | 2.8–3.1 | 3.0–4.5 |
| Isoleucine | 2.2–2.7 | 2.1–3.7 |
| Leucine | 2.8–3.8 | 2.9–6.3 |
| Methionine | 2.2–2.3 | 2.9–6.3 |
| Cystine | 1.1 | 0.6–0.8 |
| Tyrosine | 2.2–2.5 | 1.3–2.5 |
| Phenylalanine | 2.2–2.8 | 2.1–2.8 |
| Total essential Amino acids | 27.0–31.0 | 21.0–44.0 |
| Histidine | 2.2–3.7 | 2.0–3.3 |
| Arginine | 5.0–6.7 | 3.8–6.4 |
| Aspartic acid | 7.2–8.5 | 6.1–7.1 |
| Serine | 3.9–4.2 | 2.8–4.3 |
| Glutamic acid | 10.0–15.0 | 10.0–15.7 |
| Proline | 2.2–3.7 | 2.6–4.6 |
| Glycine | 3.3–3.6 | 3.4–3.8 |
| Alanine | 5.5–5.9 | 4.0–5.4 |
| Total amino acid | 66.0–82.0 | 69.0–72.0 |

Table 3 describes the Estimated Nutritive Value of *P. ostreatus* CBS 101937 fruiting bodies (FB) and submerged mycelium (M).

TABLE 3

| Protein was calculated | Protein content, % | | EAA index, (FAO) | | NI | |
| --- | --- | --- | --- | --- | --- | --- |
| | FB | M | FB | M | FB | M |
| N total × 6.25 | 17.0 | 42.0 | 80.0 | 70.0 | 14.0 | 29.0 |
| N total × 4.38 | 12.0 | 29.0 | 113.0 | 99.0 | 14.0 | 29.0 |
| Protein | 11.0 | 23.0 | 124.0 | 125.0 | 14.0 | 29.0 |

Table 4 describes the fatty acid composition of the *P. ostreatus* CBS 101937 (% of total methyl esters). The linoleic acid content in the submerged mycelium is higher than that in the fruiting bodies.

TABLE 4

| Fatty acid | Submerged mycelium | Fruiting bodies |
| --- | --- | --- |
| Myristic (14.0) | 1.5 + 0.4 | 1.3 + 0.3 |
| Palmitic (16.0) | 18.4 + 1.9 | 16.6 + 1.3 |
| Palmitoleic (16.1) | 1.5 + 0.4 | 1.1 + 0.2 |
| Oleic (18.1) | 18.4 + 1.6 | 15.2 + 1.2 |
| Linoleic (18.2) | 43.2 + 1.5 | 36.3 + 1.5 |

Table 5 describes the content of minerals in *Pleurotus ostreatus* CBS 101937 (mg/100 g dry weight). The chromium and selenium contents of the submerged mycelium are higher than those of the fruting bodies.

TABLE 5

| Minerals | Fruiting bodies | Mycelium |
| --- | --- | --- |
| Potassium | 2100–3793 | 735–1800 |
| Phosphorus | 495–1960 | 985–1980 |
| Sodium | 30–839 | 80–316 |
| Calcium | 5–292 | 40–94 |
| Magnesium | 75–590 | 148–359 |
| Sulfur | 8.3 | 2.1 |
| Iron | 3.4–33.41 | 39.1–60.0 |
| Copper | 0.3 2.2 | 0.5–2.44 |
| Zinc | 1.7–9.1 | 1.85–5.70 |
| Manganese | 0.2–36.4 | 2.0–9.0 |
| Cobalt | 0.01–0.37 | 0.01–0.36 |
| Molybdenum | 0–0.07 | 0.01–0.36 |
| Selenium ($\mu$g) | 30.3 | 0.02–0.36 |
| Chromium | 0.01–0.04 | 0.05–3.4 |
| Nickel | 0.04–0.13 | 0.05–2.9 |
| Stannous | 0.7–2.8 | 7.4–31.4 |
| Vanadium | 0–0.02 | 0.01–0.02 |
| Barium | 0–0.01 | 0.03–0.15 |
| Bor | 0.8–1.5 | |
| Titanium | 0.03–0.36 | 0.15–1.3 |
| Plumbum | 0.05–0.74 | 0.1–0.54 |
| Silver | 0.02–0.08 | 0.01–0.09 |

Table 6 describes the vitamin content in *Pleurotus ostreatus* CBS 101937 (mg/100 g dry weight). The thiamin, riboflavin and ascorbic acid levels in the submerged mycelium are higher than the levels in the fruiting bodies.

TABLE 6

| Vitamins | | Fruiting bodies | |
| --- | --- | --- | --- |
| Symbol | Compound | Wild* | Mycelium |
| B1 | Thiamine | 0.4–2.6 | 0.6–6.0 |
| B2 | Riboflavin | 1.0–3.4 | 2.6–5.7 |
| B5/PP/ | Niacin | 60.0–138.0 | 64.0–122.0 |
| B6 | Piridoxin | 0.04–0.8 | 0.06–0.47 |
| B7 | Biotin ($\mu$g) | 8.0–76.0 | 14.0–63.0 |
| B12 | Cyanobalamin | — | — |
| C | Ascorbic acid | 50.0–98.0 | 70.0–108.0 |
| D2 | Calciferol ($\mu$g) | 0.12 | 0.10–0.14 |
| Pro-D | Ergosterol | — | — |
| E | Tocopherol | 10.1 | 6.6–10.6 |
| Pro-A | Beta-carotene | — | Trace |

The present invention is not to be limited in scope by the embodiments disclosed in the example which is intended as an illustration of one aspect of the invention and it is contemplated that the scope of the invention encompasses any number of species and genera of the higher Basidiomycetes mushrooms grown in submerged culture.

What is claimed is:

1. A new and distinct variety of Basidiomycetes mushroom grown in submerged cultures, and mushroom being the species *Pleurotus ostreatus* deposited under the Budapest Treaty with Centraalbureau voor Schimmelcultures (CBS) as Acc. No. CBS 101937.

2. A new and distinct variety of Basidiomycetes mushroom grown in submerged cultures, said mushroom being of the species *Pleurotus eryngii var. ferulae* deposited under the Budapest Treaty with Centraalbureau voor Schimmelcultures (CBS) as Acc. No. CBS 101938.

* * * * *